United States Patent [19]

Neushul

[11] Patent Number: 4,783,446

[45] Date of Patent: Nov. 8, 1988

[54] METHOD FOR THE TREATMENT OF AIDS VIRUS AND OTHER RETROVIRUSES

[75] Inventor: Michael Neushul, Goleta, Calif.

[73] Assignee: Neushul Mariculture Incorporated, Goleta, Calif.

[21] Appl. No.: 18,889

[22] Filed: Feb. 25, 1987

Related U.S. Application Data

[63] Continuation-in-part of Ser. No. 801,115, Nov. 22, 1985, abandoned.

[51] Int. Cl.$^4$ ............................................. A61K 31/715
[52] U.S. Cl. ...................................... 514/54; 514/885; 514/934
[58] Field of Search ............... 424/195.1; 514/54, 885, 514/934

[56] References Cited

U.S. PATENT DOCUMENTS

| | | | |
|---|---|---|---|
| 4,162,308 | 7/1979 | Calvin et al. | 424/195.1 |
| 4,162,309 | 7/1979 | Calvin et al. | 424/195.1 |
| 4,522,814 | 6/1985 | Wonamura et al. | 514/54 |

OTHER PUBLICATIONS

Richards et al. (1978), Antiviral Activity of Extracts from Marine Algae, Antimicrobial Agents and Chemo. 14:24–30.
Deig et al. (1974), Inhib. Herpes Virus Repl. by Marine Algae Extracts, Antimicrob. Agents and Chemo., 6:524.
Blunden et al. (1981), A Survey of Some British Marine Algae for Ant–Influenza Virus Activity, Bot. Mar. 24:267.
Ehresmann et al. (1977), Antiviral Sub. from Cal. Marine Algae, J. Phycol. 13:37–40.

*Primary Examiner*—John W. Rollins
*Attorney, Agent, or Firm*—Roman Saliwanchik; David R. Saliwanchik

[57] ABSTRACT

The subject invention concerns the use of a carrageenan and other sulfated polysaccharides to treat AIDS and other infections caused by retroviruses. The invention also concerns a method for stimulating T-cell activity in humans and animals with carrageenans and other sulfated polysaccharides.

10 Claims, No Drawings

METHOD FOR THE TREATMENT OF AIDS VIRUS AND OTHER RETROVIRUSES

DESCRIPTION

This is a continuation-in-part of my copending application Ser. No. 801,115; filed on Nov. 22, 1985, now abandoned.

BACKGROUND OF THE INVENTION

Retroviruses are a relatively newly recognized group of RNA viruses. Many are associated with malignancies in mammals. The first retrovirus to be isolated, RNA tumor virus, was isolated by Rous early in this century. However, it was several decades later before it was realized that retroviruses play an important role in oncology. Pioneering work in this area included the isolation of retroviruses in laboratory mice and their subsequent linkage to murine leukemias and lymphomas (Gross, L. [Ed.] 1983, *Oncogenic Viruses.* Pergamon Press, N.Y.). Exogenous retroviruses are now linked to human malignancies, indicating that some types of cancer are infectious (Gallo, R. C.; [1984] Gallo, R. C., Essex, M. E. and Gross L. [Eds] *Human T-Cell Leukemia/Lymphoma Virus—The Family of Human T-Lymphotropic Retroviruses: Their Role in Malignancies and Association with AIDS.* Cold Spring Harbor Laboratory, Cold Spring Harbor, N.Y.). In addition, acquired immune deficiency syndrome (AIDS) is now linked to an infectious retrovirus.

AIDS is a disease that was first described in mid 1981. By Aug. 30, 1985, 12,932 cases had been reported in the United States, with 6,480 deaths. Reliable estimates suggest that as many as one million Americans have been infected with the AIDS virus to date. (Curran et al. [1985] Science 229:1352–1357). Retrovirus infections usually persist for life. The severity of this disease has placed it at the top of the health priorities of the U.S. Research on AIDS has been successful in linking this disease to a virus, human T-cell lymphotropic virus type III (HTLV-III) and to the HTLV genome itself, rather than to a minor component of the virus complex. See Gallo, R. C. et al. (1983) Science 220:865–867 and Fisher et al. (1985) Nature 316:262–265. This virus is transmitted through sexual contact, sharing contaminated needles, through blood and blood products and from infected mothers to their newborn children. Although 73% of the cases are reported as occurring in homosexual men, the number of cases diagnosed in heterosexuals is increasing rapidly. An immunodiagnostic test has been developed to detect the presence of antibodies to HTLV-III. This test has been used to detect antibody in over 90% of AIDS patients and from a high proportion of people in high-risk groups. Through the modes of infection listed above, the number of cases is expected to increase. Therefore, an epidemic is developing that could kill most of its victims.

A two-pronged strategy is being taken to treat or cure AIDS: to inhibit the virus and to build up the immune system. Research is being undertaken on developing a vaccine, although it is unknown at this time whether a safe and effective vaccine can be developed. Antiviral drugs are also being sought which would inhibit the virus or prevent infection. Dolin (Dolin, R. [1985] Science 227:1296–1303) recently reviewed the successful development of compounds for antiviral chemotherapy and chemoprophylaxis. These compounds, such as nucleoside analogs, typically block some part of the life cycle of a virus. These agents are specifically activated and incorporated by viral enzymes but are poor substrates for cellular enzymes. Therefore, these drugs interfere with viral DNA replication while not affecting the DNA replication of the host cells. Several drugs have been investigated to treat AIDS, including suramin, Fascarnet and HPA 23. The former two are antiviral drugs used for other viruses while the last is a newly developed French drug. Although these drugs may inhibit virus replication in the body, they also have hazardous side effects.

There has recently been increased interest in searching for pharmaceuticals from marine macroalgae. Hoppe et al. (Hoppe, O., Levring, T. and Tanaka, Y. [1978] *Marine Algae in Pharmaceutical Science.* W. de Gruyter, N.Y.) published a volume that reviews many of the established or potential pharmaceutical uses of marine algae. It is apparent from the papers in this book and the large volume of literature that is cited that there are many potential uses that are yet untapped. More recently, Fenical (Fenical, W. [1983] Proceedings of the Joint U.S.-China Phycological Symposium, Quingdao, China, 1981, Academia Sinica, Peoples' Republic of China) reviewed the potential for the use of marine algae as the source of pharmaceuticals and agrichemicals. Efforts have been directed at studying marine algae with antiviral activity (Ehresmann, D. W., et al. [1977] J. Phycol. 13:37–40, and Blunden, G. et al. [1981] Bot. Marina 24:267–272), with antibiotic activity (Faulkner, D. J. [1978] P. Sammes [Ed.] *Topics in Antibiotic Chemistry.* E. Horwod Publishers, Chichester, England, and Shield, L. S. and Rinehart, K. L. Jr. [1978] *Antibiotics, Isolation, Separation and Purification.* Journal of Chromatography Library, Elsevier, N.Y.), and with unique and specific cytotoxicity (Gerwick, W. H. et al. [1980] J. Amer. Chem. Soc. 102:7991–7993).

Marine algae have been screened for activity against herpes simplex virus (HSV, Ehresmann, D. W. et al. [1977] J. Phycol. 13:37–40) and influenza virus (Blunden, G. et al. [1981] Bot. Marina 24:267–272). Deig et al. (Deig, E. F. et al. [1974] Antimicrob. Ag. Chemother. 6:524–525) first reported that in vitro replication of HSV was inhibited by extracts of several marine red algae. Twenty-eight species of marine macroalgae were collected and extracts from these red algae were tested for antiviral activity (Ehresmann, D. W. et al. [1977] J. Phycol. 13:37–40). Ten of these reduced the infectiousness of HSV types 1 and 2. Studies of these extracts indicated that the active agent was a structural polysaccharide which blocked an early step in the cycle of infection, thereby restricting the spread of the virus (Ehresmann, D. W. et al. [1977] J. Phycol. 13:37–40; Hatch, M. T. et al. [1979] O. Hoppe, T. Levring and Y. Tanaka [Eds] *Marine Algae in Pharmaceutical Science.* W. de Gruyter, N.Y.). Richards et al. (Richards, J. T. et al. (1978) Antimicrob. Agents Chemother. 14:24–30) have shown that extracts of two red algae have in vivo antiviral activity in mice infected with herpes simplex virus. This research has spawned sufficient interest for several patents. Three patents have been issued for red algal treatments of herpes virus infections (U.S. Pat. Nos. 4,162,308 and 4,162,309, issued 1979 and 4,522,814, issued 1985). They claim that these red algae have shown effective treatment in humans. There is no known prior art which discloses the isolation of anti-AIDS, or anti-retroviral activity from marine algae.

In parent application Ser. No. 801,115, abandoned, I disclose and claim a novel composition of matter designated as SA-1. This material has a high degree of activity against the virus HTLV-III. Accordingly, SA-1 can be used to treat AIDS and other infections caused by retroviruses.

SA-1 is disclosed in Ser. No. 801,115 as being obtained from the well-known marine algae genus Schizymenia.

Further work on SA-1, which is now referred to as HIVA (human-immunodeficiency-antiviral), reveals that this material contains the well-known sulfated polysaccharide, carrageenan. Tests have now shown that decreasing concentrations of carrageenan correlate with decreasing levels of reverse-transcriptase inhibition using a standard test as disclosed in Ser. No. 801,115.

BRIEF SUMMARY OF THE INVENTION

The subject invention concerns the use of carrageenans and other sulfated polysaccharides to treat AIDS and other infections caused by retroviruses. The carrageenans which can be used in this invention are, for example, lambda, kappa, and iota carrageenan, and various mixtures of these compounds. The carrageenan can be in the salt form, for example, sodium, calcium, potassium, and the like. The molecular weight of the carrageenans will normally be in the range of 5,000 to about 500,000, with most being in the range of about 100,000 to 500,000.

The carrageenan can be administered systemically for treatment of retrovirus infections, including AIDS. Since the carrageenans are well-known substances used commercially in gelling, emulsifying, and as a stabilizing agent and viscosity builder in foods and non-foods, it is clear that toxicity is not a factor in their safe use in humans and animals hosting a retrovirus infection. Thus, the dosage of a carrageenan used to treat an animal or human hosting a retrovirus infection can range up to 5 gm per day for an adult, since this is within the present Food and Drug Administration recommendations for food additive carrageenan. At this level, effective anti-retroviral effects generally can be expected. Higher dosage ranges may be established once suitable testing has been completed.

DETAILED DISCLOSURE OF THE INVENTION

The carrageenans useful in the subject invention are well known and available readily from numerous commercial sources. As reported in The Merck Index, Tenth Edition, on page 260, carrageenans are found in the red seaweed (Rhodophyceae). Of course, the well-known marine algal genus Schizymenia, as disclosed in Ser. No. 801,115, is a good source for carrageenan. Procedures for recovering carrageenan from natural sources are well known, for example, as disclosed on page 260 of the Merck Index, as discussed above. This disclosure is incorporated herein by reference thereto. Further, the entire disclosure of Ser. No. 801,115 is incorporated herein by reference thereto.

Other retrovirus, oncoRNA virus, or oncovirus infections which might be treated with the composition of matter of the subject invention are human T-cell leukemia virus (HTLV), porcine leucosis virus, bovine leucosisvirus, Friend leukemia virus, lentiviruses, feline leucosis virus, the avian sarcoma viruses, and the foamy retroviruses of primates, cats, humans and bovines (spumavirus F).

The composition of matter of the subject invention also stimulates T-cell activity as shown by a standard assay. This assay involves culturing $2 \times 10^5$ Balb/c spleen cells for 72 hr with 5 µg/ml concanavalin A with T-cells. The incorporation of tritiated thymidine is used as an indication of immunocyte activity. Thus, the carrageenans of the subject invention can be used to induce the production of IL-2 by activating T-cells—IL-2 stimulates the T-cells to proliferate. As reported in Science (1983) 221:1362–1364, "Researchers from NIAID and the Food and Drug Administration (FDA), using a test tube assay, have recently found that interleukin-2 improved the function of T-cells from six AIDS patients" (p. 1362).

A method of treatment of retrovirus infections utilizing the carrageenans of the present invention can generally be by ingestion with a suitable carrier.

The carrageenans can be used for systemic treatment of retrovirus infections. Such treatment can be effected by using a carrageenan in a suitable carrier administered intravenously, by inhalation or by oral ingestion to a person infected with the retrovirus.

Fluid unit dosage forms for oral administration such as syrups, elixirs, and suspensions can be prepared wherein each teaspoonful of composition contains a predetermined amount of a carrageenan for administration. The carrageenan can be dissolved in an aqueous vehicle together with sugar, flavoring agents and preservatives to form a syrup. An elixir is prepared by using a hydroalcoholic vehicle with suitable sweetener together with a flavoring agent.

For parenteral administration, fluid unit dosage forms are prepared utilizing the carrageenan and a sterile vehicle, water being preferred.

The carrageenan, depending on the form and concentration used, can be dissolved in the vehicle. In preparing solutions, the carrageenan can be dissolved in water for injection, and filter sterilized before filling into a suitable vial or ampule and sealing. Advantageously, adjuvants such as a local anesthetic, preservative and buffering agents can be dissolved in the vehicle.

In addition to oral and parenteral administration, the rectal and vaginal routes can be utilized. The carrageenan can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing the carrageenan and a suitable pharmaceutical vehicle, water being preferred, or by dry powder for insufflation.

For use as aerosols the carrageenan can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used herein refers to physically discrete units suitable as unitary dosages for human and animal subjects, each unit containing a predetermined quantity of a carrageenan calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredient to be employed as an anti-viral agent can be easily prepared in unit dosage form with the employment of pharmaceutical materials which themselves are available in the art and can be prepared by established procedures. The quantity of anti-retroviral carrageenan suitable for various dosage forms can be determined from the anti-retroviral activity of the carrageenan.

The antiviral substance reduces the production of the essential viral enzyme, reverse transcriptase. The details of this assay have been published in the Aug. 9, 1985 issue of Science (Shinju, H. et al. [1985] "Infection of HTLV-III/LAV in HTLV-I-Carrying Cells MT-2 and MT-4 and Application in a Plaque Assay" Science 229:563–566). This publication is incorporated herein by reference thereto.

Suitable dosage adjustments can be readily made to meet the severity of the treated infection while taking into account the age, weight, and overall conditions of the host being treated.

The above systemic treatment procedures with a carrageenan also can be used to stimulate T-cell activity in a human or animal host in need of such treatment.

The carrageenans used in the invention can be substituted for by other sulfated polysaccharides having a molecular weight ranging from 5,000 to about 2,500,000.

Further uses for the carrageenans and sulfated polysaccharides of the invention are as an assay tool, for example, to use in vitro to test the efficacy of other antivirals by procedures known in the art. The compounds also can be used to coat contraceptive devices by known procedures to form an anti-retrovirus film on the device.

I claim:

1. A method of treating retrovirus infections in humans and animals which comprises treating a retrovirus-infected human or animal host with an anti-retroviral effective amount of a carrageen, or a mixture of carrageenans.

2. A method, in accordance with claim 1, wherein said retrovirus is HTLV-III.

3. A method, in accordance with claim 1, wherein said carrageenan is adapted for systemic application.

4. A method, according to claim 1, wherein said carrageenan is lambda, or kappa, or iota carrageenan.

5. A method, according to claim 1, wherein said carrageenan is in the salt form.

6. A method of treating retrovirus infections in humans and animals which comprises treating a retrovirus-infected human or animal host with an anti-retroviral effective amount of a sulfated polysaccharide.

7. A method for stimulating T-cell activity in humans and animals comprising administering to a human or an animal, in need of T-cell stimulation, a T-cell stimulating effecive amount of a carrageenan, or a mixture of carrageenans.

8. A method, in accordance with claim 7, wherein said carrageenan is adapted for systemic application.

9. A method, according to claim 7, wherein said carrageenan is lambda, or kappa, or iota carrageenan.

10. A method, according to claim 7, wherein said carrageenan is in the salt form.

* * * * *

Notice of Adverse Decisions in Interference

In Interference No. 102,137, involving Patent No. 4,783,446, M. Neushul, METHOD FOR THE TREATMENT OF AIDS VIRUS AND OTHER RETROVIRUSES, final judgement adverse to the patentee was rendered July 31, 1990, as to claims 1-10.

[*Official Gazette October 23, 1990*]